(12) United States Patent
Laing et al.

(10) Patent No.: US 10,341,204 B2
(45) Date of Patent: Jul. 2, 2019

(54) METHODS AND APPARATUS FOR DEVICE MANAGEMENT

(71) Applicant: Under Armour, Inc., Baltimore, MD (US)

(72) Inventors: Scott Laing, Austin, TX (US); Marissa Dessanti, Austin, TX (US); Brian Carden, Austin, TX (US); Marcus Piña, Austin, TX (US); Andrew Moore, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 421 days.

(21) Appl. No.: 14/938,489

(22) Filed: Nov. 11, 2015

(65) Prior Publication Data

US 2017/0134249 A1    May 11, 2017

(51) Int. Cl.

| | | |
|---|---|---|
| G06F 15/16 | (2006.01) |
| H04L 12/26 | (2006.01) |
| H04L 29/08 | (2006.01) |
| A61B 5/024 | (2006.01) |
| A61B 5/11 | (2006.01) |
| A61B 5/00 | (2006.01) |
| G01G 19/50 | (2006.01) |
| A61B 5/0205 | (2006.01) |
| G06F 19/00 | (2018.01) |
| G16H 40/67 | (2018.01) |
| H04W 4/38 | (2018.01) |
| H04W 4/80 | (2018.01) |

(52) U.S. Cl.
CPC .......... *H04L 43/065* (2013.01); *A61B 5/0022* (2013.01); *A61B 5/024* (2013.01); *A61B 5/0205* (2013.01); *A61B 5/1118* (2013.01); *A61B 5/4806* (2013.01); *A61B 5/4866* (2013.01); *G01G 19/50* (2013.01); *G06F 19/00* (2013.01); *G16H 40/67* (2018.01); *H04L 43/0817* (2013.01); *H04L 67/22* (2013.01); *H04W 4/38* (2018.02); *H04W 4/80* (2018.02); *A61B 5/681* (2013.01); *A61B 2560/0204* (2013.01); *A61B 2560/0242* (2013.01)

(58) Field of Classification Search
CPC ...................................... H04L 43/065
See application file for complete search history.

(56) References Cited

U.S. PATENT DOCUMENTS

| | | |
|---|---|---|
| 8,180,591 B2 | 5/2012 | Yuen et al. |
| 8,775,120 B2 | 7/2014 | Molettiere et al. |
| 8,849,610 B2 | 9/2014 | Molettiere et al. |
| 8,909,264 B1 * | 12/2014 | Higuchi .......... H04W 4/00 455/456.3 |

(Continued)

*Primary Examiner* — Moustafa M Meky
*Assistant Examiner* — SM Z Islam

(57) ABSTRACT

Apparatus and methods are provided for managing a plurality of user devices. In one exemplary embodiment, a unified user interface is provided which is configured to display to a user status information and frequency of use information regarding a plurality of health monitoring devices associated to the user. Such a unified interface assists the user in building healthy habits, meeting health-related goals, and ensuring that the user's devices are well maintained. The display is derived from information obtained and processed at a management entity in communication with the plurality of health monitoring devices.

20 Claims, 8 Drawing Sheets

(56) References Cited

U.S. PATENT DOCUMENTS

| | | | |
|---|---|---|---|
| 8,949,022 B1 | 2/2015 | Fahrner et al. | |
| 9,084,536 B2 | 7/2015 | Yuen et al. | |
| 9,224,171 B2* | 12/2015 | Peak | G06Q 40/08 |
| 2008/0109684 A1* | 5/2008 | Addleman | G06F 11/3419 |
| | | | 714/47.2 |
| 2011/0060378 A1* | 3/2011 | Tuysserkani | A61N 1/39 |
| | | | 607/5 |
| 2012/0081230 A1* | 4/2012 | Sullivan | G08B 21/24 |
| | | | 340/636.1 |
| 2013/0041590 A1 | 2/2013 | Burich et al. | |
| 2013/0226486 A1 | 8/2013 | Henderson et al. | |
| 2013/0312066 A1* | 11/2013 | Suarez | G06F 19/3418 |
| | | | 726/4 |
| 2014/0273858 A1 | 9/2014 | Panther et al. | |
| 2015/0018991 A1 | 1/2015 | Arnold et al. | |
| 2015/0066172 A1 | 3/2015 | Yi | |
| 2015/0100141 A1 | 4/2015 | Hughes | |
| 2015/0182797 A1 | 7/2015 | Wernow et al. | |

* cited by examiner

METHODS AND APPARATUS FOR DEVICE MANAGEMENT

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

The present disclosure relates to the field of device management. More particularly, the present disclosure relates to methods, devices, systems, and computer programs for the management of a plurality of user devices via a unified user interface.

BACKGROUND

The background description provided herein is for the purpose of generally presenting the context of the disclosure. Unless otherwise indicated herein, the materials described in this or any section of the disclosure are not prior art to the claims in this application and are not admitted to be prior art by inclusion herein.

Recent advancements in electronics technology has led to the widespread use of portable devices. In particular, a large variety of biometric monitoring devices that users may wear on their bodies to measure activity (e.g., a number of steps taken, flights of stairs, hours of sleep, etc.), biometric parameters (e.g., hear rate, blood pressure, etc.), and other environmental parameters (e.g., temperature, altitude, etc.) have become widely available for general use. Accordingly, data may be provided to the user from this vast variety of devices.

The data provided from the plurality of user devices creates a significant problem to the user with regard to data management. Moreover, as the number of devices increases, it becomes increasingly difficult for the user of the devices to monitor the status of each device (e.g., battery/power level, remaining memory, connection/signal strength, etc.). Hence, what are needed are methods, devices, systems, and computer programs for the management of a plurality of user devices and the establishment of healthy and helpful patterns of use for each via a unified user interface.

SUMMARY OF THE DISCLOSURE

The present disclosure addresses the foregoing needs by disclosing, inter alia, methods, devices, systems, and computer programs for the management of a plurality of user devices via a unified user interface.

Specifically, methods, apparatus, computer applications, and systems are provided to manage a plurality of health devices via: assignment of a unique identifier to each of a plurality of health devices connected to a management entity; receipt of status information from individual ones of the plurality of health devices; determination of a value configured to represent a level correlation between the received status information and stored status information which is specific to respective ones of the individual ones of the plurality of health devices; and display of a notification selected based at least in part on the determined value.

These and other aspects of the disclosure shall become apparent when considered in light of the disclosure provided herein.

BRIEF DESCRIPTION OF THE DRAWINGS

Embodiments will be readily understood by the following detailed description in conjunction with the accompanying drawings. To facilitate this description, like reference numerals designate like structural elements. Embodiments are illustrated by way of example, and not by way of limitation, in the figures of the accompanying drawings.

All Figures© Under Armour, Inc. 2015-2016. All rights reserved.

DETAILED DESCRIPTION

Exemplary Embodiments

Disclosed embodiments include systems, apparatus, method and storage medium associated with device management in general, and unified user interface in particular.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

Figure 1:
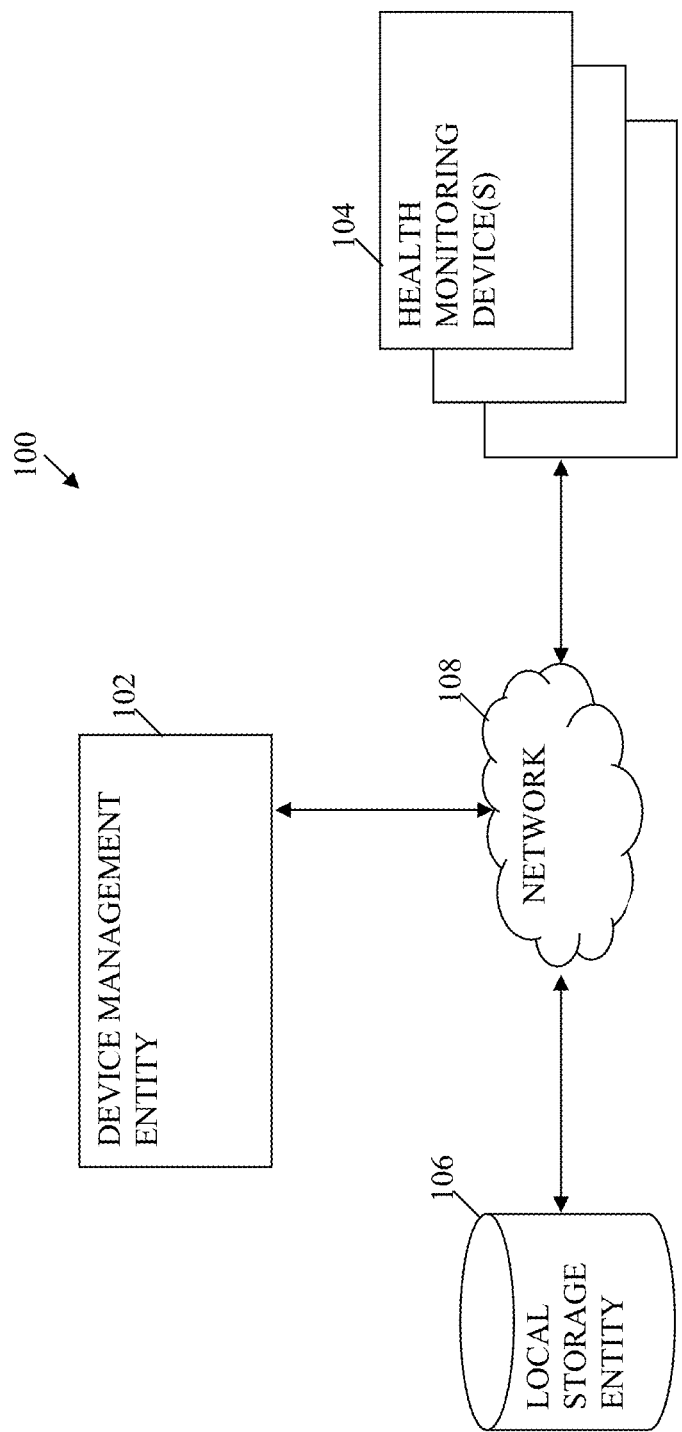
FIG. 1 is a block diagram illustrating an exemplary device management system in accordance with one embodiment of the present disclosure.

Referring now to FIG. 1, an exemplary device management system 100 in accordance with one embodiment of the present disclosure is illustrated. As shown, the system 100 generally comprises a device management entity 102 in communication with a plurality of health monitoring devices 104 via a network 108.

The device management entity 102 may comprise a software application or suite of applications configured to run on a client device whether stationary or portable. For example, the management entity 102 may run on desktop computers (such as those available from Dell Computing of Austin, Tex.), or smartphones, computing tablets, laptop computers, electronic readers, personal digital assistants, and so forth, such as Galaxy S4® from Samsung Electronics of Seoul, Korea, or iPad® from Apple Computer of Cupertino, Calif.

The plurality of monitoring devices 104 may comprise one or more portable computing devices designed to measure, sense, or monitor biometric, environmental, and/or activity parameters. In one variant, certain ones of the health monitoring devices 104 comprise wearable health-related parameter measurement and computing devices, such as e.g., a smart watch, an activity tracker, a heart rate monitor, a sleep tracking device, a nutrition tracking device, a smart scale, and/or smart eyeglasses. In addition, an exemplary monitoring device 104 may comprise a smart phone having one or more of the foregoing monitoring capabilities. In a further embodiment, the management entity 102 may be configured as an application suite configured to run on an individual one of the plurality of monitoring devices 104 (such as e.g., a smart phone).

The monitoring devices 104 provide sensed data and status information to the management entity 102 via the network 108. The sensed data comprises data which the particular device 104 is configured to collect (such as activity, biometric, and environmental data). For example, an activity tracking device is configured to collect activity data such as steps taken, distance traveled, rate or pace of a run, and/or flights of stairs climbed, etc.; a heart rate monitor is configured to collect heartbeat data; a sleep tracking device collects data relating to how much time a user/wearer spends sleeping; a nutrition tracking device collects data relating to food and drinks consumed by a user; a smart scale collects data relating to a body weight, body fat percentage, and/or body mass index (BMI), etc. Furthermore, a smart watch and/or smart phone, may be utilized as an activity tracking device, a heart rate monitor, a sleep tracking device, and/or a nutrition tracking device. The sensed data is provided to the management entity 102 as it is collected, i.e., in real time. Alternatively, sensed data may be provided as a single so-called "data dump" at a predetermined time for each monitoring device 104.

The network 108 which enables communication between the device management entity 102 and the monitoring devices 104 may comprise a wired and/or wireless, private and/or public network, including e.g., the Internet. Accordingly, each of the monitoring devices 104 and the device management entity 102 may be configured with an appropriate networking communication interface(s). An example of wired communication interface may include, but is not limited to, Ethernet; while examples of wireless communication interfaces may include, but are not limited to, near field communication (NFC), Bluetooth, WiFi, 4G or 5G LTE. It is further appreciated that various gateways, routers, switches, based stations, and so forth may be placed between the communication interfaces of foregoing devices.

As discussed in greater detail below, upon a start-up of a new health monitoring device 104, the device 104 is registered to the management entity 102. In another alternative, the management entity 102 may periodically or upon its start-up look for monitoring devices 104 within the network 108 and/or physically nearby. Once registered, the management entity 102 will continue to make attempts to connect to and communicate with the device 104 (unless or until the device is de-registered). Irrespective of the manner in which it occurs, during a first communication between a monitoring device 104 and the management entity 102, the management entity 102 assigns a unique identifier to the monitoring device 104.

In one embodiment, the unique identifier corresponds to a vendor/Ethernet/Bluetooth/Mac address, serial number, and/or other identifier of the device 104. Alternatively, the user may (via a user interface) enter a unique identifier to each monitoring device 104, e.g., "ACTIVITY TRACKER", "BODY ANALYZER", etc. In a further example, the management entity 102 may assign the unique identifier without additional input or information.

The unique identifier is provided to the monitoring devices 104 so that all messages or data received therefrom may be associated to the appropriate device. Accordingly, the management entity 102 is able to properly identify data received from an individual one of the monitoring devices 104 to that particular monitoring device 104. Similarly, messages may be routed to the appropriate devices 104 using the unique identifiers.

The management entity 102 stores the information relating each device 104 to its unique identifier at a local storage entity 106. In one embodiment, the local storage entity 106 comprises a separate device from the management entity 102. Alternatively, the storage entity 106 may be integrated within the management entity 102. In addition, the storage entity 102 stores device specific standards for each of the health monitoring devices 104 which may be pre-loaded therein, or provided thereto via an Internet database (not shown).

In yet another embodiment, the storage entity 106 stores information received from a device data warehouse into which device manufacturers place device-specific data, such as status standards and/or use thresholds. This information may then be provided to the device management entity 102 and/or to the local storage entity 106 via a data push/pull. Updates to this information may be requested by the management entity 102 periodically, pushed automatically, and/or the manufacturer may push a notification to the storage entity 106 to collect updated information at the device data warehouse.

Figure 2:
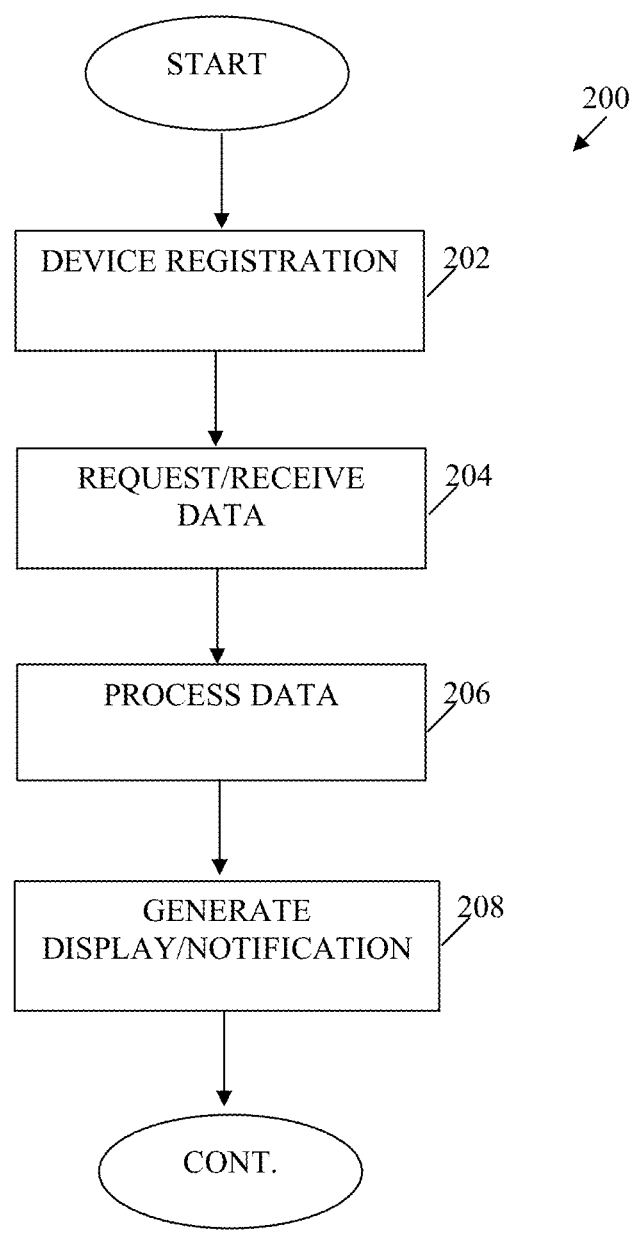
FIG. 2 is a logical flow diagram illustrating a generalized method for managing devices in accordance with one embodiment of the present disclosure.

Referring now to FIG. 2, a generalized method 200 for device management according to the present disclosure is provided. As shown, the method 200 generally comprises registration of a plurality of monitoring devices 104 at step 202. As noted previously, the registration may occur at start-up of a new monitoring device 104 or the management entity 102, and/or may be due to a periodic request from the management entity 102. The device registration at step 202 further includes assignment of a unique identifier to each of the monitoring devices 104 which are to be managed. The unique identifiers are then used in communications between the management entity 102 and the devices 104 to ensure appropriate identification thereof.

Next at step 204, data is requested and/or received from the plurality of health monitoring devices 104. In one embodiment, the data received from a monitoring device 104 comprises health or status information about the device itself. For example, the device 104 may provide information relating to an amount of power (e.g., battery) or memory remaining at the device 104, etc. Alternatively or in addition, the data received from the monitoring device 104 may comprise sensed or monitored data regarding a wearer or user of the device 104. For example, the device may provide information relating to a number of steps taken, a heart rate, an amount of sleep, a number of calories ingested, a weight of the user, environmental conditions during a workout, etc. The management entity 102 processes the data at step 206 and appropriate displays and/or notifications are provided at step 208. A more detailed discussion of processing of each of the foregoing categories of data collected at step 204 (device status data and sensed or monitored data) is provided below at FIGS. 3 and 4, respectively.

Exemplary notifications may include, e.g., notices to plug in or charge a device, to re-connect a device, to move data from a device to external storage, to use a device (such as when the device has not been used recently or frequently enough).

Figure 3:
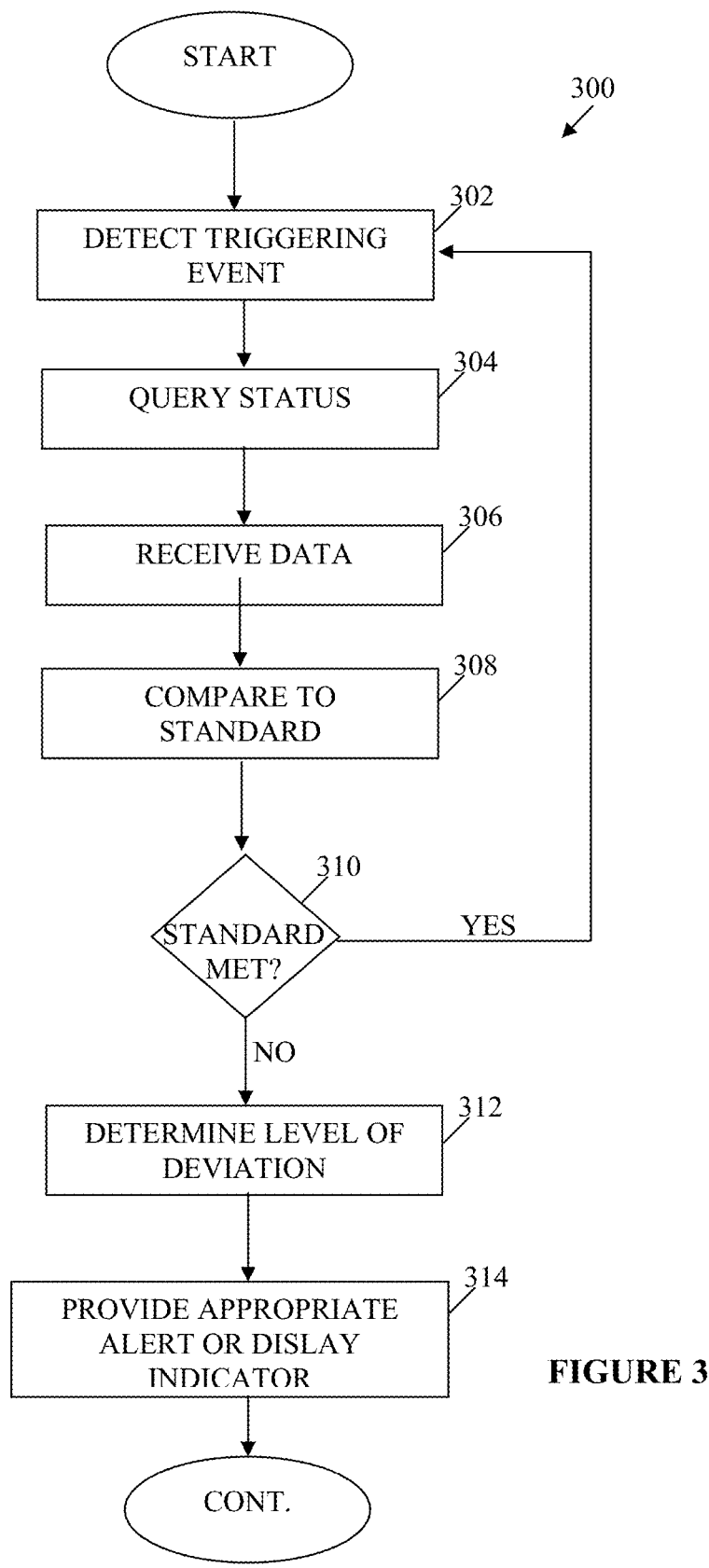
FIG. 3 is a logical flow diagram illustrating one exemplary method for managing a status of each of a plurality of devices in accordance with the present disclosure.

Referring now to FIG. 3, an exemplary method 300 for managing a status of each of a plurality of devices is shown. As discussed above, each of the health monitoring devices 104 is registered to the management entity 102 and assigned a unique identifier which is used in subsequent communication between the management entity 102 and the monitoring device 104, such as the communications discussed subsequently herein.

As illustrated, per step 302 a triggering event is detected. In one embodiment, the triggering event is based on a running clock. For example, the method 300 may occur periodically at timed intervals; thus, the triggering event comprises an expiration of the period or interval. In another embodiment, the triggering event may comprise a log-in or start-up of the management entity 102. Still further, the triggering event may comprise a re-start (such as a hard boot) or a return from a loss of signal event.

Upon detection of the triggering event (step 302), a status query message is transmitted from the management entity 102 to one or more of the plurality of monitoring devices 104 connected thereto. In one embodiment, the status query message is provided to all devices 104 irrespective of the most recent last status thereof. In another embodiment, the query message may only be provided to those ones of the plurality of monitoring devices 104 that have experienced a high priority status (as discussed below) in a most recent query and/or that have had a high priority status (e.g., an unfavorable status) for longer than a threshold period of time.

The status query message is configured to request from the receiving monitoring devices 104 information relating to a status thereof. For example, the message may request current power level information from the devices. In another example, the message may request current unused memory amount. In a further example, the message may request information relating to a data rate, signal strength, and/or connection strength. A response to the request for status information is received at the management entity 102 at step 306. The foregoing messages and responses are merely exemplary and do not represent the entirety of possible device status information which may be shared between the management entity 102 and the monitoring devices 104; rather, virtually any type of status information may be requested and/or received.

Next, at step 308, a process running at the management entity 102 is utilized to compare the received status information of each monitoring device 104 to standard data. The standard data may comprise pre-loaded data, derived data, and/or data provided by a device manufacturer. In addition, the standard data may take into account historical data and/or information entered by a user or operator of the management entity 102 (in the form of so-called 'user preferences').

In yet another embodiment, the management entity 102 is configured to estimate a status based on a previous status and a time since a last status query. For example, if a battery or power remaining in a device 104 was near empty at a last status query, and the pattern of behavior of that device is known to drain more power than remained, the system may estimate that the power has been depleted. Moreover, the management entity 102 may derive status patterns based on recorded behavior over time. For instance, the management entity 102 may determine that a particular device will lose half its power after 12 hours, and will be fully depleted after 24 hours, and therefore may provide status updates and/or notifications to a user without necessarily querying the device 104.

When it is determined that a standard for the status information is met (step 310), the method repeats at step 302. When it is determined that the standard for the status information is not met (step 310), an amount of deviation from the standard is determined at step 312, and an appropriate display/indicator or notification is provided based on the determined amount of deviation from the standard. In a further embodiment, the selection of an appropriate notification may take into account user-entered preferences for receiving such notification, and/or the amount of time the device 104 has spent in a high priority status (i.e., unfavorable status).

In one specific example, the status information comprises power level. According to this example, the current power level is provided from each monitoring device 104 to the management entity 102 in response to a request for the same. The current power level is compared to for example, stored/saved standard power information. If the current power is equal to the standard, then the standard is met and the display remains unchanged. In this case, the standard may comprise an amount representative of full power; hence, display would indicate that the full power standard is met. Alternatively, the standard may indicate a "safe" power amount which may be significantly less than full power. If the current power differs from the provided standard power, a difference therebetween is calculated. In this manner, the system is able to determine how far the device 104 is away from full power or a "safe" limit. For example, various ranges maybe given to correlate with low, medium and high deviation from the standard. In one exemplary embodiment, the deviation may be displayed to a user or operator of the management entity 102 in the form of a status or health bar chart which is filled-in according to the deviation level and which may additionally be color coded. Specifically, high correlation of current power to standard may be represented as a fully filled bar with color green, medium correlation of current power to standard may be represented as a half-filled bar with color yellow, and low correlation of current power to standard may be represented as a nearly empty bar with color red. Another embodiment may utilize a series of icons representative of each of the monitored device statuses, when a high priority, error or non-favorable condition is identified, the icons are illuminated or otherwise brought to the user's attention. A user may alter this notification scheme according to his/her preferences, such as to increase/decrease priority ranges.

Similarly, when the status information comprises a memory amount and/or connectivity or signal strength, the current status is compared to standard information and displayed in one embodiment as a status bar. In this manner, memory and/or signal strength for each device 104 may be reflected as high, medium and low in a status bar. However, other mechanisms for displaying status may be utilized with equal success. The device status information may include additional factors, the foregoing being merely exemplary.

Figure 4:
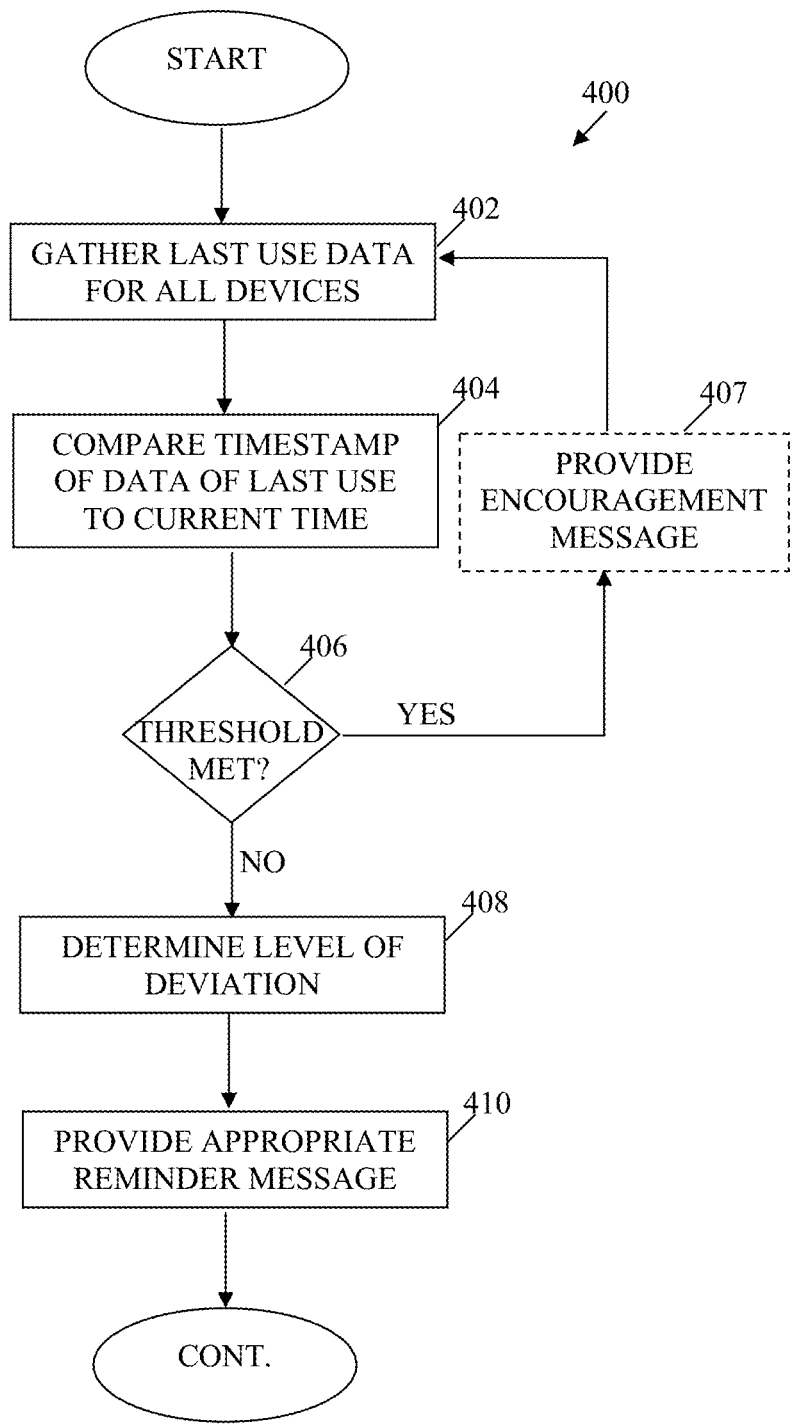
FIG. 4 is a logical flow diagram illustrating one exemplary method for managing use of each of a plurality of devices in accordance with the present disclosure.

Referring now to FIG. 4, an exemplary method 400 for managing use of each of a plurality of devices is shown. As discussed above, each of the health monitoring devices 104 is registered to the management entity 102 and assigned a unique identifier which is used in subsequent communication between the management entity 102 and the monitoring device 104, such as the communication discussed subsequently herein.

As illustrated, per step 402, data is gathered regarding the last instance of use of each of the health monitoring devices 104. In one embodiment, the monitoring entity 102 specifically queries each device 104 of a date/time of last use periodically; alternatively, the date/time of last use of each device 104 may be transmitted periodically by the monitoring devices 104 without an express request therefor by the management entity 102. In another exemplary embodiment, the monitoring entity 102 may simply review sensed data records (i.e., the records which were received from the devices 104 regarding the activity which was sensed thereat). As noted above, the sensed data may be provided in real-time or as a periodic data dump (such as daily, weekly, etc.), however the individual data records may comprise a date/time stamp which indicates a precise date/time at which the data was sensed or collected, and which therefore may be referred to as a date/time of last use.

At step 404, the timestamp of the last instance of use data (i.e., data collected at step 402) is compared to a current time. A threshold level of similarity is provided either by a user/operator, the management entity 102, devices 104, and/or by the device manufacturer. The threshold level indicates an appropriate time range for utilization of each device 104. The threshold may, for example, be representative of a determination that a particular monitoring device 104 functions best to estimate a user's overall health when it is used at a certain periodicity (e.g., daily, at every meal, weekly, etc.), and that after a certain period of non-use (e.g., hours, days, weeks, etc.) it is improbable that a user will become constant or habitual user. Alternatively, a user him/herself may make the above threshold determinations (i.e., use goals) and enter appropriate thresholds for each monitoring device 104 which are stored at e.g., the local storage entity 106. When a threshold level of similarity is met (step 406), an encouragement message is optionally provided to the user at step 407. In another embodiment, when the threshold is met, the method 400 returns to step 402 and continues. When the threshold is not met (step 406), then per step 408, a level of deviation from the threshold is determined and an appropriate reminder message is provided (step 410). In one variant, the level of deviation relates to the priority level of the reminder message provided such that, as the deviation away from the threshold increases, the priority or intensity of the message increases.

The aforementioned encouragement and reminder messages may comprise messages designed by a user him/herself. For example, via a user interface, a user may type or record (such as using video and/or audio) a message which should be displayed or provided to the user when the threshold is met (i.e., an encouragement message) and/or when the threshold is not met (i.e., a reminder message). In addition or alternatively the user may or a process running on the management entity 102 may select from among a plurality of standard messages for encouragement and/or reminders (including hierarchal reminders to be selected based on the level of deviation from the threshold as discussed above). Once again, these messages may include text, audio, and/or visual. In another variant, the messages may be recorded by certain celebrities or athletes.

In yet another embodiment, the management entity 102 is configured to derive patterns of behavior of the user with respect to particular devices. For example, it may be determined that when the device is used at least four days in a row, the user is 80% more likely to continue using the device every day for at least three weeks. Hence, on day four of consecutive use, the management entity 102 may remind the user to use the device and therefore cause the fourth consecutive day (thereby increasing the likelihood that the user will practice at least three weeks of additional consecutive use).

In one exemplary embodiment, an activity tracking device 104 may have preset threshold (entered by the user, the management entity 102, and/or a manufacturer of the activity tracking device) that it should be used daily with a deviation of three days. Accordingly, when the timestamp data indicates a date/time of last use as compared to a current time of one day, an encouragement message may be provided. In this manner, the user is encouraged/rewarded for consistent use of the activity tracking device. Additional rewards (such as messages, badges, etc.) may be further provided when a consistent pattern of use is demonstrated as well. When the timestamp data indicates a date/time of last use as compared to a current time of more than one day, e.g., two days, a reminder message may be provided. In this manner, the user is reminded to utilize the activity tracking device. Moreover, as the deviation approaches three days, the reminder message may be more intense and/or may be provided more frequently. It is appreciated that the user may further enter preferences for such notifications and timing thereof.

Figure 5:
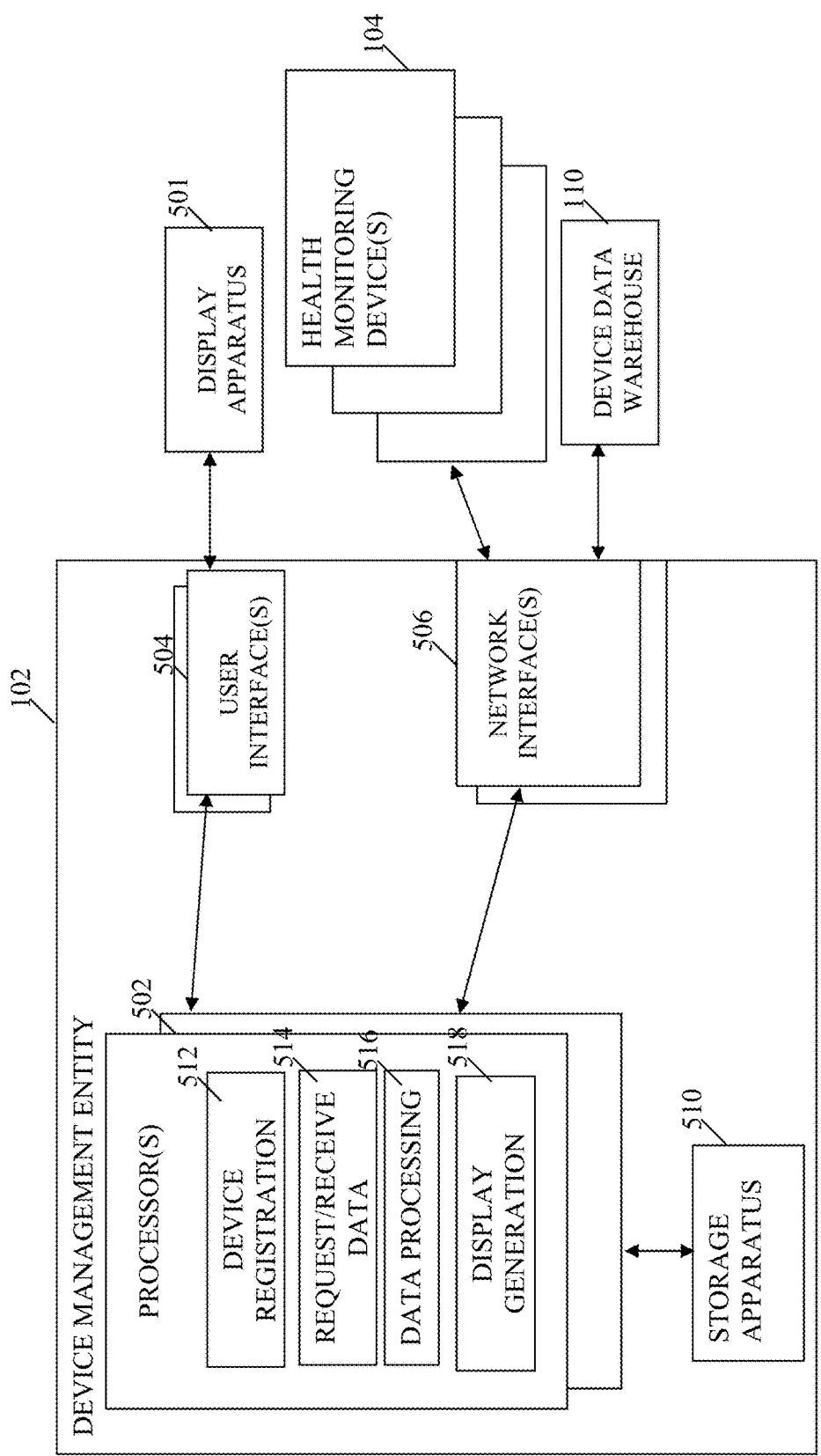
FIG. 5 is a block diagram illustrating an exemplary device management entity in accordance with one embodiment of the present disclosure.

Referring now to FIG. 5, an exemplary device management entity 102 is given. As shown, the device management entity 102 generally includes a storage apparatus 510 and one or more processors 502, user interfaces 504, and network interfaces 506. Other components of the management entity 102 may additionally be provided to ensure functioning of the management entity 102 (not shown). In one embodiment the storage apparatus 510 corresponds to the local storage entity 106 of FIG. 1. Alternatively, the local storage entity 106 may comprise a separate entity than the management entity 102 (yet may be in communication therewith), and the storage apparatus 510 comprises a temporary storage facility for quick use by the management entity 102.

The user interfaces 504 comprise means by which a user can interact with various ones of the applications or programs on the management entity 102. In one embodiment, a graphic user interface (GUI) is displayed to the user via a display apparatus 501, which may be located within the device management entity 102 or separate therefrom. For example, the GUI may be displayed on a display screen of a smart phone (in this example, the smart phone comprises the device management entity 102). Exemplary GUI are illustrated at FIGS. 6A-6F and will be discussed in further detail below.

The network interfaces 506 enable communication between the health monitoring devices 104 and the device management entity 102. Additionally, the network interfaces 506 enable communication between the device management entity 102 and network devices via the network 108 such as e.g., a device manufacturer. In one embodiment, the network interfaces 506 comprise a dedicated communication line between each health monitoring device 104 and the management entity 102 (such as via dedicated frequency bands, etc.); alternatively other well-known mechanisms may be utilized to enable communication over a shared connection.

The management entity 102 further includes one or more processors or processor cores 502 configured to run various computer applications thereon, which may be stored at e.g., the storage apparatus 508. For the purpose of this application, including the claims, the terms "processor" and "processor cores" may be considered synonymous, unless the context clearly requires otherwise. Additionally, the storage apparatus 508 may include mass storage devices such as diskette, hard drive, compact disc read only memory (CD-ROM) and so forth. Additional features of the management apparatus 102 may include e.g., input/output devices (such as display, keyboard, cursor control and so forth) and additional communication interfaces (such as network interface cards, modems and so forth), not shown. Moreover, the elements may be coupled to each other via system bus including one or more bridged busses (not shown).

The computer applications run by the processor 502 include one or more of: a device registration application 512, a data request/receive application 514, a data processing application 516, and a display generation application 518. Additional software applications and processes may be run at the processors 502 as well; the foregoing are merely exemplary. Moreover, the functionality described as attributable to one or more of the foregoing applications may be combined into fewer applications and/or a single application.

In one exemplary embodiment, the device registration application 512, the data request/receive application 514, the data processing application 516, and the display generation application 518 are run as a management application suite on a computerized device (such as a smartphone) and cooperate to provide the functionality described throughout the disclosure.

The device registration application 512 comprises a software process which enables the plurality of health monitoring devices 104 to register with the monitoring entity 102. As discussed above, the registration process 512 may specifically enable the management entity 102 to identify or be notified of new monitoring devices 104 as they enter the network 108 and subsequently assign a unique identifier to each device 104. Thereafter, communication between the management entity 102 and the devices 104, including inter alia communication of sensed or monitored data relating to a user's measured health characteristics and/or status information relating to the devices 104 themselves, is identified via the unique identifier. In this manner, the management entity 102 is able to properly associate all communications received from an individual one of the monitoring devices 104 to that particular monitoring device 104. Additionally, the unique identifier will assist in routing messages to the individual monitoring devices 104.

The data request/receive application 514 comprises a software process which enables the monitoring entity 102 to request and receive data from the monitoring devices 104. The request/receive application 514, for example, may cause periodic requests for data to be sent to the devices 104 for device status information, and/or sensed or monitored information. In addition, the request/receive application 514 enables the monitoring entity 102 to request and receive information from other entities via the network 108.

The data processing application 516 comprises a software process which enables the management entity 102 to process data. For example, the processing application 516 may enable processing of sensed data to determine a date/time of last use of a particular device 104; the date/time of last use is then processed via the processing application 516 to determine whether a threshold for last use is met and to select which, if any, notifications, alerts, reminders, and/or messages should be sent to a user. In addition, the processing application 516 may process status data to determine whether standards therefor have been met and provide appropriate notifications to a user (such as by directing changes to a display for the status of particular devices 104). It is further noted that the processing application 516 is configured to take into account user-entered preferences regarding notifications including e.g., frequency of delivery, and events which would trigger sending notifications. Alternatively, the management entity 102 may control the timing of notifications based on the use frequency threshold and/or amount of time spent in a non-favorable status.

The display generation application 518 causes generation of the GUI which is displayed to a user of the management entity 102. As noted elsewhere herein, changes to the GUI may be based on decisions made by the processing application 516. For example, the processing application 516 may determine that a particular notification should be displayed, this determination is sent to the display generation application 518 which then causes the display to be changed to display the particular notification.

In other embodiments, the foregoing applications (514, 516, and 518) may be a launched via a generic browser, such as Internet Explorer, available from Microsoft Corp., of Redmond, Wash., or Safari from Apple Computer of Cupertino, Calif., e.g., such as in cases where management device 102 comprises a desktop or tablet computer. In other embodiments, the applications (514, 516, and 518) may comprise client side applications, e.g., in cases where management device 102 comprises a personal digital assistant or smartphone. In such cases, the applications are stored at a storage apparatus 106 independent or separate from the management device 102 itself.

A permanent copy of the programming instructions for the aforementioned applications (514, 516, and 518) may be placed into permanent storage devices (such as e.g., the storage apparatus 508 and/or storage entity 106) during manufacture of the management device 102, or in the field, through e.g., a distribution medium (not shown), such as a compact disc (CD), or through communication interface 506 (from a distribution server (not shown)). That is, one or more distribution media having an implementation of the agent program may be employed to distribute the agent and program various computing devices.

The herein described application suite (i.e., applications 514, 516, and 518) improves the functioning of the management device 102 by enabling it to provide a unified user interface which enables a user/operator to monitor the status of each device and date/time of last use thereof. Furthermore, devices that are able to collect data regarding a status and last use of devices in order to determine a priority of notification can operate more efficiently to indicate to a user important device health/status information and establish healthy lifestyle patterns.

Figures 6A, 6B:
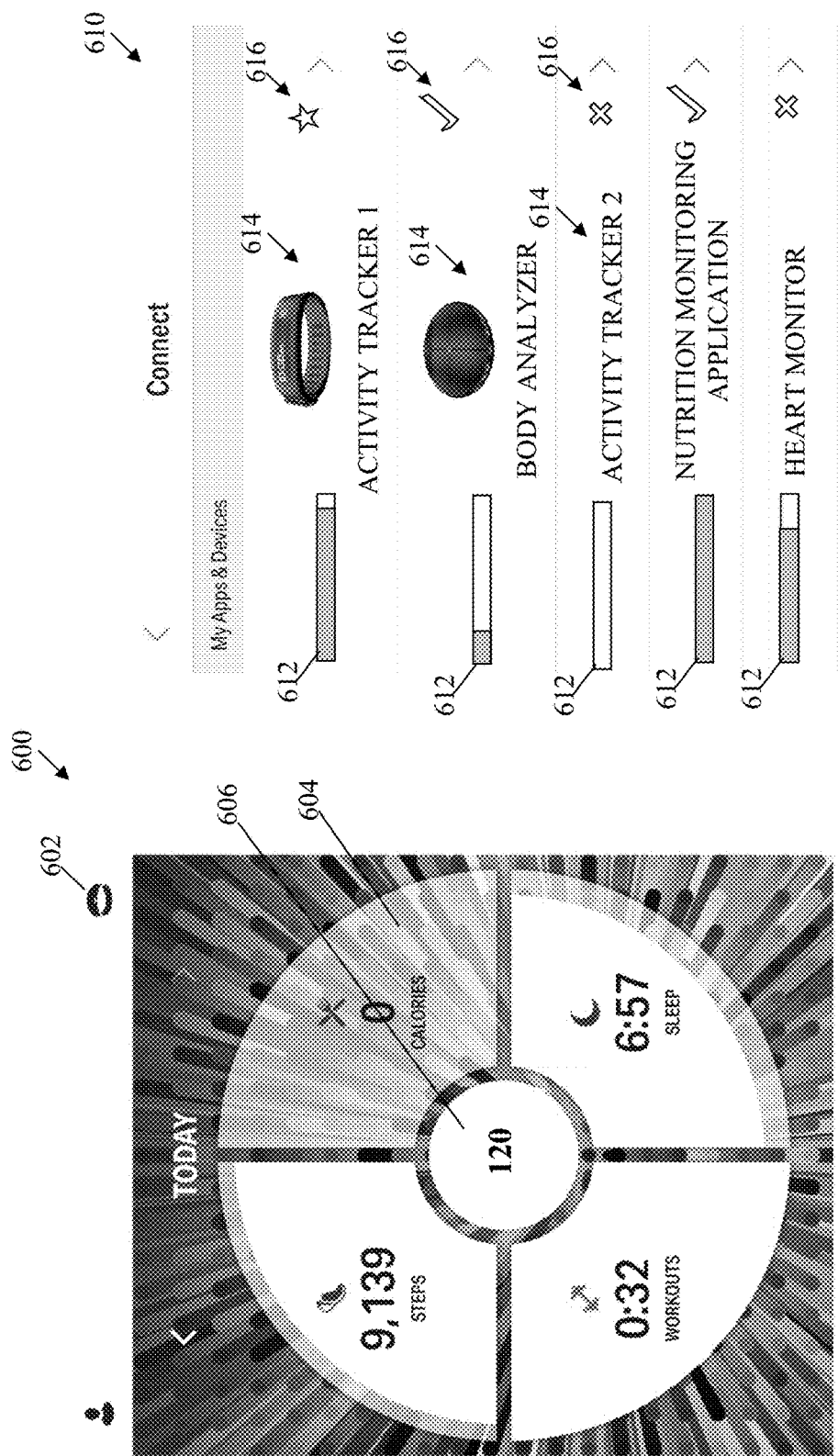
FIG. 6A is a graphical representation of an exemplary user interface showing a home screen according to one embodiment of the present disclosure.
FIG. 6B is a graphical representation of an exemplary user interface showing a device management screen according to one embodiment of the present disclosure.

FIGS. 6A-6F comprise exemplary user interfaces to be displayed by the management entity 102. Specifically, FIG. 6A illustrates an exemplary so-called "home screen" 600 to which a user is brought when the management application suite (i.e., an application which utilizes the component applications 514, 516, and 518 discussed above) is loaded or launched. As shown, the home screen 600 includes one or more indicator panels 604 which each relate to sensed or monitored data.

The goal panels 604 in the present embodiment include panels to display actual goals, progress toward goals, and/or current amount for: total number of steps taken, calories consumed, amount of time spent in workouts, and amount of sleep. The home screen 600 of the illustrated embodiment, further includes a central indicator panel 606. As illustrated, the central panel 606 may display a goal weight, progress to a goal weight (e.g., 5 lbs to go), and/or a current weight. In yet another embodiment, the central panel 606 may display a selectable icon which, when selected, directs the user to a new screen (not shown) which indicates e.g., current weight, progress toward a goal weight, and/or goal weight.

Figure 6D:
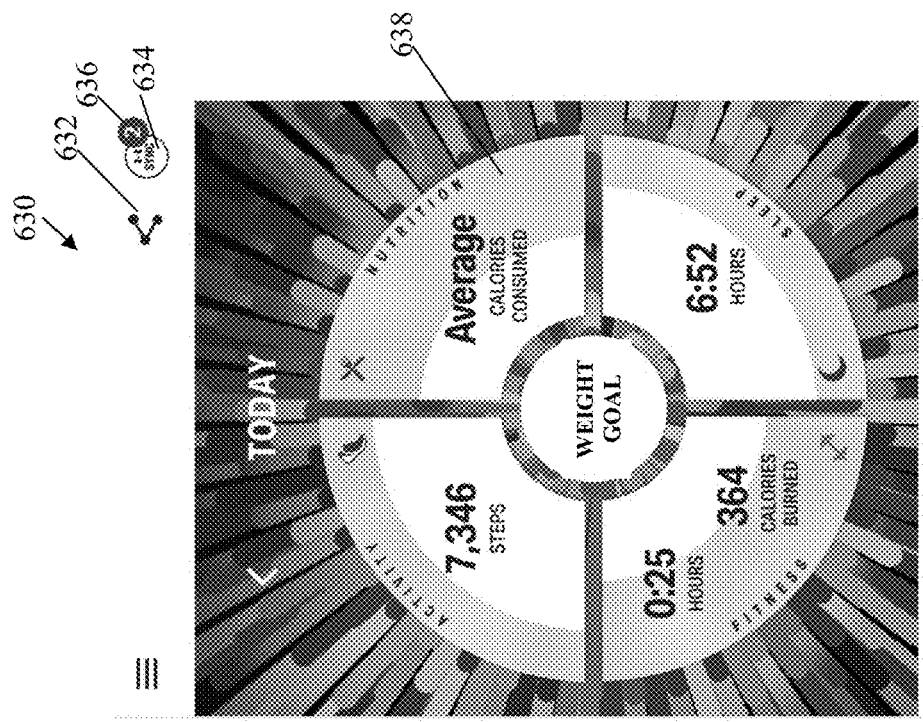
FIG. 6D is a graphical representation of an exemplary user interface showing a home screen according to another embodiment of the present disclosure.
Figure 6C:
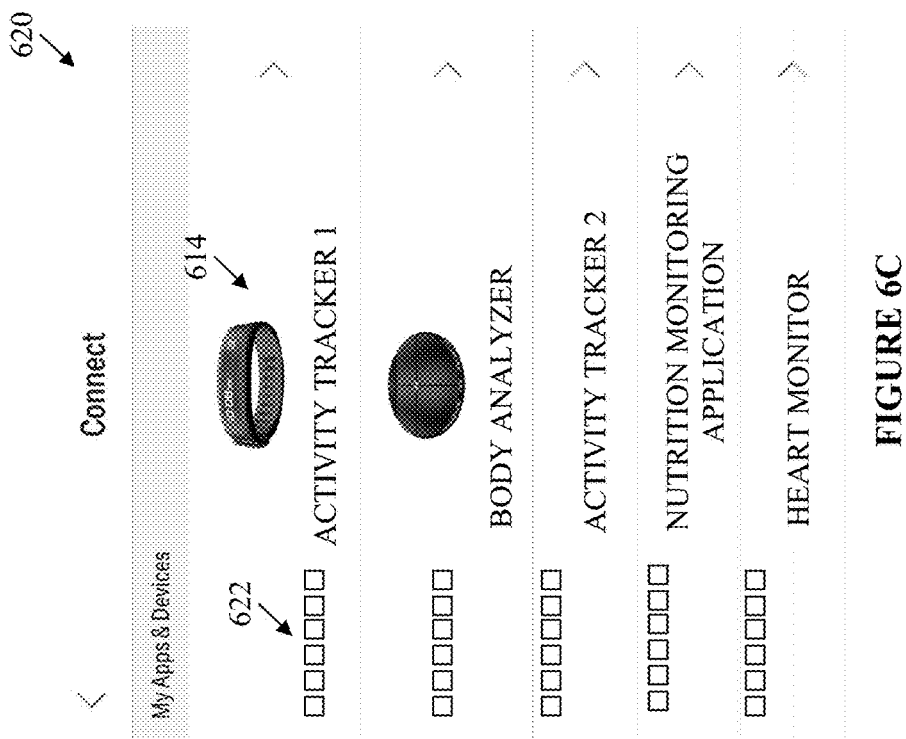
FIG. 6C is a graphical representation of an exemplary user interface showing a device management screen according to another embodiment of the present disclosure.

The home screen 600 further includes a selectable icon 602 which a user may select in order to be directed to the device management screen 610 (FIGS. 6B, 6C, and/or 6F). In the illustrated embodiment, the icon 602 comprises a figure representative of one of the managed health monitoring devices 104. Alternatively, the icon 602 may comprise a generic device icon and/or a selectable description of the device management functionality.

At FIG. 6B, an exemplary device management screen 610 is illustrated. As shown, the device management screen 610 comprises a unified list of health monitoring devices 104 and various status indicators for each.

Specifically, each entry in the list comprises a device status bar 612, a device descriptive portion 614, and a use indicator 616. The device status bar 612, in the illustrated embodiment, is a graphical representation of at least one device status as compared to a standard. The device descriptive portion 614 may comprise text and/or images which represent each of the plurality of monitoring devices 104. Finally, the use indicator 616 comprises an image or other indicator of the use status of the device. Each of these will be described in further detail below.

The device status bar 612 in the embodiment of FIG. 6B comprises a shaded bar. In one example, the amount of shading corresponds to an amount of remaining power in a particular device 104. The amount of remaining power in the device 104 may be derived by the management entity 102 using the methods and software processes discussed above. For example, as discussed above with respect to FIG. 3, the shading of the status bar 612 may be representative of whether the standard data is met and/or a determined deviation therefrom. Hence, when standard data for full power is met, the status bar 612 will be shown as completely shaded; when standard data for full power is not met, and the deviation from the standard is fifty percent, the status bar 612 will be shown as half shaded; and so forth. In other alternative embodiments, several status bars 612 may be utilized, each one representing a different device status (e.g., power, memory, connection, etc.). Still further, colors may be utilized to indicate a priority of a device status (e.g., green, yellow, red), such as a colored shading on the status bar 612.

In yet another embodiment, a single status indicator may be utilized to show an overall health rating of the device 104 which takes into account several device status characteristics. Such indicator may be selectable or telescoping such that when selected, a new screen (not shown) is displayed which indicates the precise reason for the indicator (i.e., the particular one or more device status characteristics which are currently less than favorable).

In addition, the foregoing systems and methods may be utilized to indicate to a user that updates to a device's firmware and/or software are available. Such methods would indicate the available update via a less than favorable status indicator as discussed herein.

The device descriptive portion 614 in the illustrated embodiment comprises a text description of each of the monitoring devices 104. The text descriptions may be entered by a user, may be obtained from information pulled from the device manufacturer, and/or may be preloaded at the management entity 102. Stock images may also be obtained for certain ones of the monitoring devices 104. The stock images may be obtained from e.g., the device manufacturer, preloaded at the management entity 102, the results of an Internet search, and/or provided by the user.

The use indicator 616 in the embodiment of FIG. 6B comprises a badge or icon. In one example, the particular badge or icon corresponds to a frequency of use of a particular device 104. The frequency of use of the device 104 may be derived by the management entity 102 using the methods and software processes discussed above. For example, as discussed above with respect to FIG. 4, the specific use indicator 616 selected for display may be representative of whether the use threshold for that device 104 is met and/or a determined deviation therefrom. Hence, when the use threshold is met, the icon 616 may comprise a check mark; when the use threshold is not met, and the deviation from the threshold is significant, an "x" may be used as the icon 616. In instances where the deviation is even more significant, a different icon 616 may be utilized, such as a frowning or angry face, an exclamation point, etc. Additionally, in instances where the use threshold is met consistently, the badge 616 may reflect a reward status, such as a smiling face, a star, a colored ribbon (where certain colors are earned over extended use periods), etc.

As shown, the first entry on the list illustrated in FIG. 6B comprises an activity tracker. The activity tracker is identified via a text representation ("ACTIVITY TRACKER 1") and an image of the device 614. The status bar 612 for the activity tracker indicates that the power (or the memory or other status) is near full. Lastly, the use indicator 616 for ACTIVITY TRACKER 1 comprises a star icon, thereby signifying that the user has consistently met the threshold of use for the activity tracker.

Next, a body analyzer or smart scale is listed. The body analyzer is identified via a text representation ("BODY ANALYZER") and an image of the device 614. The status bar for the body analyzer indicates that the power (or memory, or other status) is nearly empty. The use indicator 616 shows a check mark, therefore signifying that the user has at least met the use threshold for this device.

A second activity tracker is illustrated next. The empty status bar 612 indicates that the device has run out of power (or memory, or other). Additionally, the "x" icon 616 indicate that the user has not met the use threshold for this device. With respect to the nutrition monitoring application, the indicated status shows full or complete power, memory, or other status with threshold use being met. Finally, the heart monitor shows nearly full power (memory, or other) and less than threshold use.

Referring now to FIG. 6C, another embodiment of an exemplary device management screen 620 is illustrated. In this embodiment, the device management screen 620 comprises a unified list of health monitoring devices 104. Specifically, each entry in the list comprises a device status bar a device descriptive portion 614, and plurality of indicator icons 622. The device descriptive portion 614 may comprise text and/or images which represent each of the plurality of monitoring devices 104. In the illustrated embodiment, the device descriptive portion 614 for certain ones of the devices comprises a text description which may be entered by a user, obtained from information pulled from the device manufacturer, and/or preloaded at the management entity 102. Other ones of the listed devices 104 include stock images, which may be obtained from e.g., the device manufacturer, preloaded at the management entity 102, the results of an Internet search, and/or provided by the user.

Figure 6F:
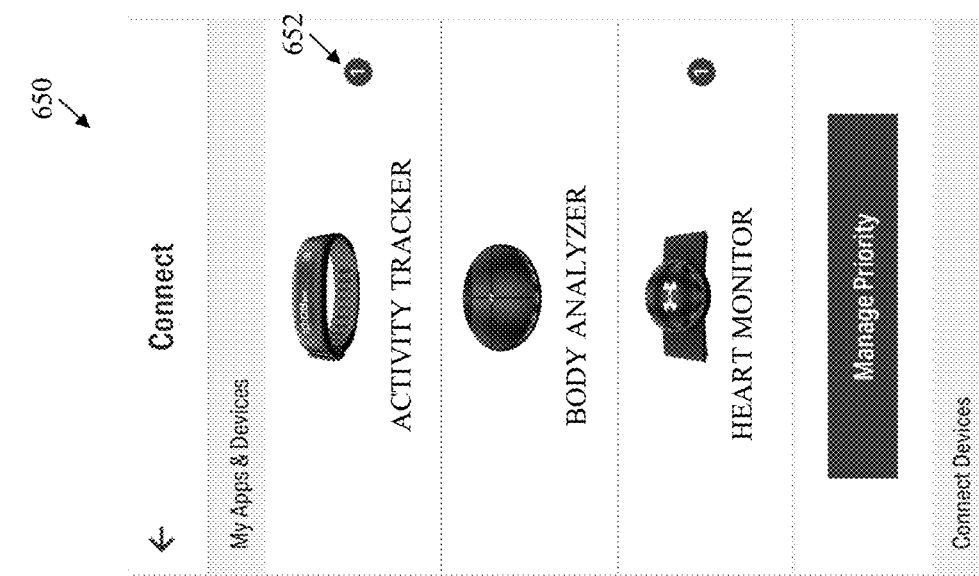
FIG. 6F is a graphical representation of an exemplary user interface showing a device management screen according to yet another embodiment of the present disclosure.
Figure 6E:
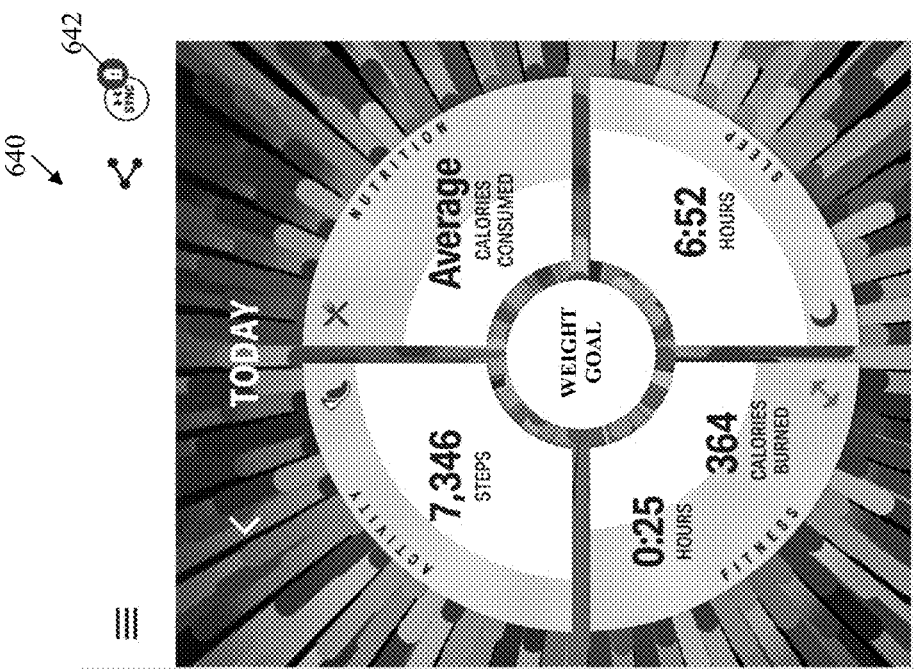
FIG. 6E is a graphical representation of an exemplary user interface showing a home screen according to yet another embodiment of the present disclosure.

Additional embodiments of an exemplary home screens 630, 640 to which a user is brought when the management application suite (i.e., an application which utilizes the component applications 514, 516, and 518 discussed above) is loaded or launched are illustrated in FIGS. 6D-6E. As shown in the embodiment of FIG. 6D, a connectivity icon 632 and a selectable device management icon 634 are given. The connectivity icon 632 may be illuminated when one or more devices are connected to the herein described application suite. In another embodiment, the connectivity icon 632 may be a selectable icon, which, when selected enables a user to manage aspects of connectivity to the connected devices. In a further embodiment, the connectivity icon 632 may display an indicator (such as those discussed elsewhere herein) which alerts an operator that one or more of the devices to which the application suite should be connected is having a connectivity issue (such as loss of connectivity, decreased connection signal, etc.).

The selectable device management icon 634 in the illustrated embodiment, comprises a manufacturer or company logo or other term which describes the management functionality. Irrespective of the text or image used, the function of the icon 634 is similar to that of the selectable icon 602 of FIG. 6A; i.e., a user selects the icon 634 in order to be directed to a device management screen 610, 620, 650 (FIGS. 6B, 6C, and/or 6F).

FIG. 6D further illustrates at item 636 an alert icon. The alert icon 636 in the present embodiment comprises a badge having a number which represents the number of notifications or alerts the user should attend to upon selection of the device management icon 634. For example, if two of the connected devices have software updates available, the number two (2) may be displayed at 636. Any combination of number and types of alerts may utilize this badge style of notifications.

It is further noted that the display panels 638 of the home screen 630 illustrated at FIGS. 6D-6E provide additional information than those of the home screen 600 of FIG. 6A. Specifically, the display panels 638 provide a text description of what is being monitored in the panel (e.g., "ACTIVITY", "NUTRITION", "FITNESS", "GOAL WEIGHT", AND/OR "SLEEP"). Additionally, an icon or image for each of the monitored parameters is also given (e.g., a shoe, a fork and knife, a dumbbell, and/or a moon). It is appreciated that alternative text and images may be displayed as well. Additionally of note, the display panels 638 of the illustrated example give supplemental information regarding the monitored parameter. Specifically, in the illustrated embodiment, the fitness panel displays not only the amount of time in a workout, but also an estimate of the number of calories burned during the workout. Still further, as shown in FIG. 6D, the nutrition panel may show the average number of calories consumed (such as per meal, per day, per week, etc.).

FIG. 6E illustrates a similar embodiment. However, in this example the selectable device management icon 634 is shown with a power alert badge 642. The badge 642 comprises an icon or image of a battery having an exclamation point inside it and is used to indicate that one or more of the connected devices 104 has a low power issue. According to this embodiment, the user will select the device management icon 634 (such as by touch on a touch screen device) to be taken to a device management screen (such as that of FIGS. 6B, 6C, and/or 6F) in order to identify the device(s) 104 which are showing a low power notice.

FIG. 6F is a graphical representation of an exemplary user interface showing a device management screen 650 according to yet another embodiment of the present disclosure. As discussed above with respect to the embodiments of FIGS. 6B and/or 6C, the device management screen 650 comprises a unified list of health monitoring devices 104 and various status indicators for each. In the present embodiment, the status indicator is illustrated as a numeric icon 652 to the right of the description and image representative of the device 104. The number in the numeric icon 652 represents a number of alerts relating to that particular device. In one embodiment, the user may select the icon 652 and/or the description or image of the device to be taken to an alert screen (not shown) which details the alerts and provides further instruction or enables the user to correct the issue (such as by downloading updated software). In a further embodiment, the icon 652 comprises an image icon, such as the previously referenced battery, an exclamation point, a star, a check mark, etc.

Although illustrated as separate embodiments, it is appreciated that any of the functions and displays of FIGS. 6A-6F may be utilized in combination with one another. For example, the battery badge icon 642 may be utilized when the only notification is a power issue, however when additional devices are in need of attention, the badge may change to a number as illustrated in FIG. 6D. In another embodiment, the home screen may display a series of icons each representative of one of the monitored device statuses (e.g., a battery icon to represent power, a plug icon to represent connectivity, a star or exclamation point icon or number badge to represent whether firmware updates are available, etc.). Then, when a high priority, error or non-favorable condition is identified, the icon for that status is illuminated or otherwise brought to the user's attention. For example, when low power is detected, the battery icon may be illuminated.

In summary, a method of managing a plurality of health devices is disclosed. In one embodiment, each of the plurality of health devices is associated to a single user. In another embodiment, the method comprises (i) causing the plurality of health devices to be connected to a management entity; (ii) the management entity assigning a unique identifier to each of the plurality of health devices; (iii) sending a request to each of the plurality of health devices, the request comprising a request for information relating to a status of each of the plurality of health devices; (iv) receiving from each of the plurality of health devices the information relating to the status, the information comprising at least a first data segment configured to indicate the status and a second data segment comprising the unique identifier; (v) processing the first data, the act of processing comprising comparing the first data segment to stored data relating to an individual one of the plurality of health devices identified by the second data segment, and determining a deviation therefrom; and (vi) causing display to the user of information relating to the determined deviation.

In addition, an apparatus for management of a plurality of health devices is disclosed. In one embodiment, the apparatus comprises: at least one interface configured to enable communication with the plurality of health devices; a storage entity; and a processor configured to communicate to the storage entity and the at least one interface. In one variant, the processor is configured to execute at least one computer program thereon, the computer program comprising a plurality of instructions which are configured to, when executed by the processor, cause the apparatus to: (i) assign a unique identifier to each of the plurality of health devices connected thereto; (ii) send a request for device status information to each of the plurality of health devices; (iii) receive from individual ones of the plurality of health devices the device status information; (iv) determine a value configured to represent a level correlation between the device status information and stored status information specific to respective ones of the individual ones of the plurality of health devices; and (v) cause display of a notification selected based at least in part on the determined value.

Furthermore, a non-transitory, computer readable medium is disclosed. In one embodiment, the non-transitory, computer readable medium comprises a plurality of instructions which are configured to, when executed: (i) connect a plurality of monitoring devices to a management entity; (ii) receive first information relating to one or more characteristics of a user monitored by individual ones of the plurality of monitoring devices, the first information including at least timestamp data; (iii) receive second information relating to a status of individual ones of the plurality of monitoring devices; (iv) compare the timestamp data of the first information to a current time to determine a period of inactivity, and when the period of inactivity exceeds a threshold, providing a notification the user; and (v) compare the second information to stored status information specific to the individual ones of the plurality of monitoring devices, and provide a display of the comparison to the user.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method of managing a plurality of health devices, each of said plurality of health devices being associated to a single user, said method comprising:
    causing said plurality of health devices to be connected to a management entity;
    said management entity assigning a unique identifier to each of said plurality of health devices;
    sending a request to each of said plurality of health devices, said request comprising a request for information relating to a status of each of said plurality of health devices;
    receiving from each of said plurality of health devices said information relating to said status, said information comprising at least a first data segment configured to indicate said status and a second data segment comprising said unique identifier;
    processing said first data, said act of processing comprising performing a comparison to determine a deviation of said first data segment from stored data relating to an individual one of said plurality of health devices identified by said second data segment; and
    causing a display apparatus to display to said user information relating to said determined deviation.

2. The method of claim 1, wherein said health devices comprise at least one of:
    a heart rate monitor;
    an activity tracking device;
    a smart scale;
    a sleep tracking device; and/or
    a nutrition tracking apparatus.

3. The method of claim 1, wherein said status of said plurality of health devices comprises a status relating to a remaining power level; and said stored data comprises data relating to an optimum power level for each of said plurality of health devices.

4. The method of claim 1, wherein said status of said plurality of health devices comprises a status relating to a remaining memory amount; and said stored data comprises data relating to an optimum memory amount for each of said plurality of health devices.

5. The method of claim 1, wherein said status of said plurality of health devices comprises a status relating to a quality of a connection to said management entity; and said stored data comprises data relating to an optimum connection quality between each of said plurality of health devices and said management entity.

6. The method of claim 1, wherein said status of said plurality of health devices comprises a date and/or time of last use by said user.

7. The method of claim 6, wherein said stored data comprises data indicative of an optimum use frequency of each of said plurality of health devices.

8. The method of claim 1, wherein said health said management entity comprises a smart phone configured to run a computer program thereon.

9. A method of managing a plurality of health devices, each of said plurality of health devices being associated to a single user and connected to a management entity, said method comprising:
   said management entity assigning a unique identifier to each of said plurality of health devices;
   receiving from each of said plurality of health devices information relating to a status thereof, said information comprising at least a first data segment configured to indicate said status and a second data segment comprising said unique identifier;
   comparing said first data segment received from an individual one of said plurality of health devices identified by said second data segment to stored data relating to said individual one of said plurality of health devices; and
   causing a display apparatus to display to said user an indication of a determined deviation of said status from said stored data.

10. The method of claim 9, wherein said management entity further comprises said display apparatus.

11. The method of claim 9, wherein said plurality of health devices comprise at least one of:
   a heart rate monitor;
   an activity tracking device;
   a smart scale; and/or
   a sleep tracking device.

12. The method of claim 9, wherein said status of said plurality of health devices comprises a status relating to a remaining power level; and said stored data comprises data relating to an optimum power level for each of said plurality of health devices.

13. The method of claim 9, wherein said status of said plurality of health devices comprises a status relating to a remaining memory amount; and said stored data comprises data relating to an optimum memory amount for each of said plurality of health devices.

14. The method of claim 9, wherein:
   at least one of said plurality of health devices comprises an activity monitor;
   said device status information comprises a current power level of said activity monitor; and
   said value is determined via a comparison of said current power level and an optimum power level for said activity monitor.

15. The method of claim 9, wherein:
   at least one of said plurality of health devices comprises an activity monitor;
   said device status information comprises a date/time of last use thereof by said user; and
   said value is determined via a determination of an amount of time elapsed between said date/time of last use thereof by said user to a current date/time, compared to an optimum use frequency.

16. The method of claim 15, wherein:
   when said value indicates that said use frequency is lower than said optimum use frequency, said notification comprises a reminder message; and
   when said value indicates that said use frequency is equal to or higher than said optimum use frequency, said notification comprises a congratulatory message.

17. A non-transitory, computer readable medium comprising a plurality of instructions which are configured, when executed by a processor of a smart phone apparatus, to:
   assign a unique identifier to each of a plurality of health devices in communication therewith, each of said plurality of health devices and said smart phone being associated to a single user;
   receive from each of said plurality of health devices a respective plurality of data packages, each data package comprising at least a first data segment configured to indicate a status of said respective one of said plurality of health devices, and a second data segment comprising said unique identifier of said respective one of said plurality of health devices;
   compare said status of each of said plurality of health devices to stored data for each of said plurality of health devices; and
   cause a display apparatus of said smart phone to display to said user an indication of a determined deviation of said status from said stored data.

18. The computer readable medium of claim 17, wherein said comparison of said status to said stored data comprises utilization of said first data segment to identify said status, and said second data segment to identify an individual one of said plurality of health devices based on said unique identifier; and said stored data comprises one of a plurality of data, each of said plurality of data associated to individual ones of said plurality of health devices, respectively.

19. The computer readable medium of claim 17, wherein at least one of said plurality of health devices comprises an activity monitor; and wherein
   said comparison comprises at least one of:
      a comparison of a current power level and an optimum power level for said activity monitor; or
      a comparison of an amount of time elapsed between said date/time of last use thereof by said user to a current date/time, compared to an optimum use frequency.

20. The computer readable medium of claim 19,
   when said comparison indicates that said use frequency is lower than said optimum use frequency, said notification comprises a reminder message; and
   when said comparison indicates that said use frequency is equal to or higher than said optimum use frequency, said notification comprises a congratulatory message.

* * * * *